Figure 1:
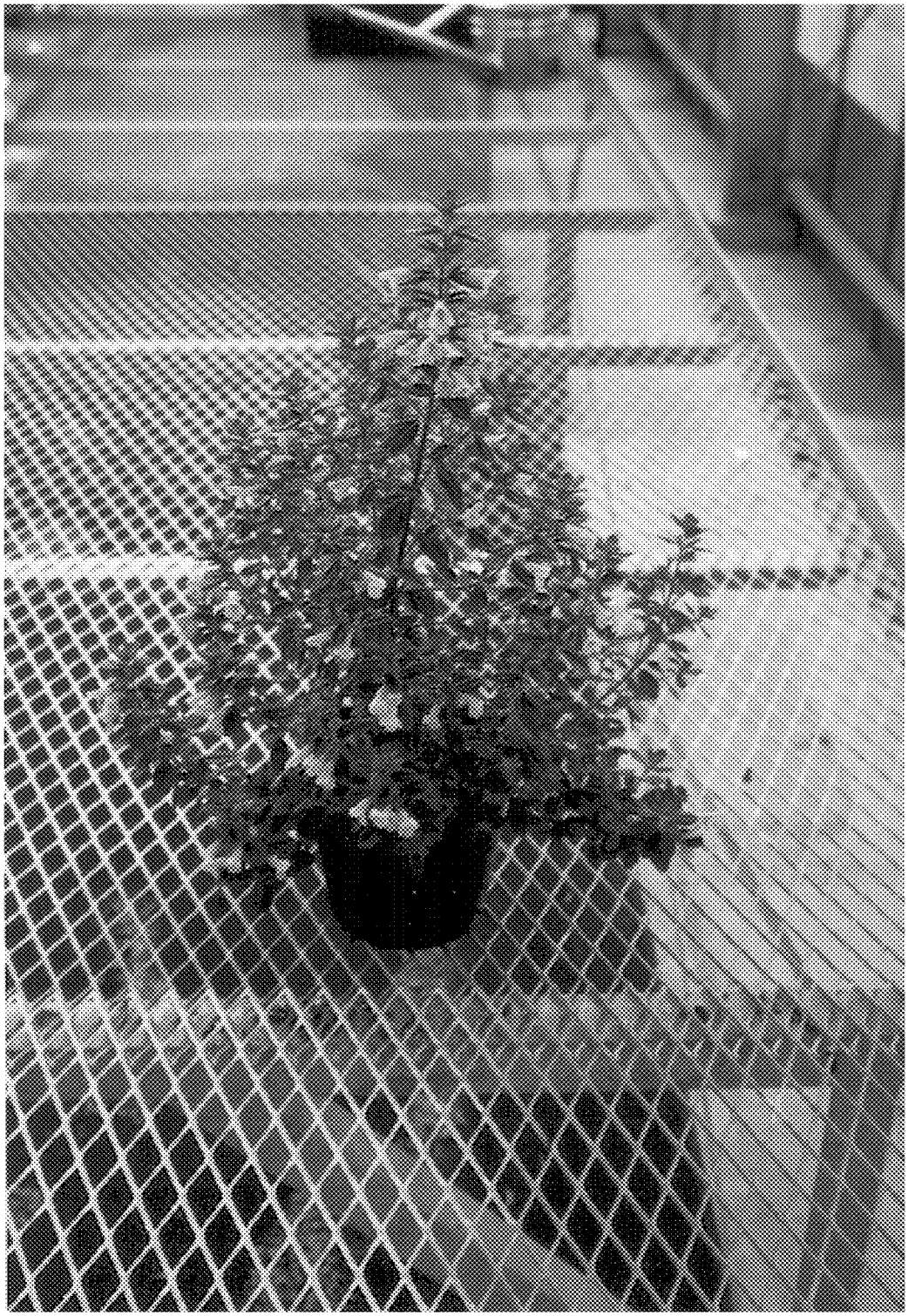

US00PP11677P

United States Patent [19]

Misato

[11] Patent Number: Plant 11,677

[45] Date of Patent: Dec. 12, 2000

[54] HESPEROZYGIS PLANT NAMED 'SUNMINBU'

[75] Inventor: Tomoya Misato, Youkaichi, Japan

[73] Assignee: Suntory Limited, Osaka, Japan

[21] Appl. No.: 09/055,248

[22] Filed: Apr. 6, 1998

[51] Int. Cl.[7] ..... A01H 5/00

[52] U.S. Cl. ..... Plt./226

[58] Field of Search ..... Plt./226, 373, 263

[56] References Cited

PUBLICATIONS

Epling, Carl and Wm. S. Stewart, A Revision of Hedeoma with a Review of Allied Genera, pp. 12 and 13 (1939).
Index Kewensis, Oxford University Press, 1997.
Epling and Mathias, Brittonia, pp. 302 and 303, 1957.
Bulletin of the Torrey Botanical Club, vol. 67, pp. 1, 509–512, Jan. 1940.
Epling, Carl and Carlos Jativa Brittonia, vol. 15, pp. 366–377, Oct. 1963.

*Primary Examiner*—Howard J. Locker
*Assistant Examiner*—Wendy A Baker
*Attorney, Agent, or Firm*—Burns, Doane, Swecker & Mathis, L.L.P.

[57] ABSTRACT

A new and distinct variety of *Hesperozygis myrtoides*× *Hesperozygis dimidiata* plant named 'Sunminbu' is provided. The plant exhibits a conical growth habit with abundant branching. The attractive light purple blossoms possess a fragrance similar to mint and are verticillaster borne in the upper leaf axils commonly with three flowers per axil. The young stems are green and change to brown with maturity. The new variety propagates well by the use of cuttings and is particularly well suited for growing as an ornamental pot plant.

2 Drawing Sheets

BACKGROUND OF THE VARIETY

The present invention relates to a new and distinct variety of *Hesperozygis myrtoides*×*Hesperozygis dimidiata*.

The Hesperozygis genus plant is rear and has not been used as a garden variety. There are only a few wild varieties of plants of the Hesperozygis genus. In general, plants of the Hesperozygis genus are flowering shrub-like perennials with labiate corollas. However, plants of the Hesperozygis genus are easy to cultivate and are well suited for growing in the garden. Accordingly, this invention was aimed at obtaining a new plant of the Hesperozygis genus for use as a garden plant having a dense branching habit, the ability to form an abundance of blossoms, and good tolerance to heat and cold.

Initially, 4 seedlings were obtained from crossing a *Hesperozygis myrtoides* plant named '1136' (non-patented in the United States) as seed parent and a *Hesperozygis dimidiata* plant named '971' (non-patented in the United States) as the pollen parent in 1994. From these 4 seedlings, one seedling was selected in 1995 in view of a great profusion of flowers. The selection was carried out in a trial planting. The botanical characteristics of the plant were examined using the parent varieties '1136' and '971' for comparative purposes from spring, 1996 to summer, 1997. As a result, it was concluded that the new plant of the present invention is distinguishable from any other variety, whose existence is known to us. It is uniform and stable in its characteristics, and has been named 'Sunminbu'.

In the following description, the color-coding is in accordance with the R.H.S. Colour Chart of The Royal Horticultural Society, London, England, and the Japan Color Standard for Horticultural Plants (J.H.S. Color Chart).

The botanical characteristics of the female parent '1136' plant are as follows:

Plant:

*Plant from.*—Conical.

*Plant height.*—Approximately 200 mm.

Branches:

*Branch color.*—Moderate yellow green (R.H.S. 146D, J.H.S. No. 3511) on young branches, brown (R.H.S. 165A, J.H.S. No. 1608) on mature branches, and tan (R.H.S. 165C, J.H.S. No. 1911) on very old branches.

*Branch texture.*—Smooth to slightly rough on young branches, and slightly rough on mature branches and very old branches.

*Lenticels.*—Absent.

*Density of branching.*—Extensive.

*Length of internode.*—Approximately 10 mm.

Leaf:

*Phyllotaxis.*—Opposite.

*Leaf shape.*—Elliptic-Oblanceolate.

*Shape of leaf margin.*—Obtuse serrate.

*Leaf attaching angle to stem.*—Horizontal.

*Leaf length.*—Approximately 12 mm.

*Leaf width.*—Approximately 22 mm.

*Color of leaf upper side.*—Dark olive green (R.H.S. 137A, J.H.S. No. 3707).

*Color of leaf reverse side.*—Moderate yellow green (R.H.S. 146B, J.H.S. No. 3514).

*Leaf thickness.*—Approximately 0.5 mm.

*Hair density on a leaf upper side.*—Sparse.

*Petiole length.*—Approximately 2.0 mm.

*Leaf fragrance.*—Present; similar to mint.

Flower:

*Inflorescence type.*—Verticillaster.

*Length of spike/Cluster.*—Approximately 30 mm.

*Length of flower interval.*—Approximately 2.6 mm.

*Number of flowers in inflorescence.*—Approximately 30.

*Corolla form.*—Lobed and bilabiate.

*Vertical diameter of flower.*—Approximately 11 mm.

*Horizontal diameter of flower.*—Approximately 10 mm.

*Length of flower.*—Approximately 24 mm.

*Length of corolla tube.*—Approximately 21 mm.

*Width of corolla tube.*—Approximately 5 mm.
*Inside color of upper part of upper labium.*—Deep reddish purple (R.H.S. 78A, J.H.S. No. 8907).
*Inside color of middle part of upper labium.*—Strong reddish purple (R.H.S. 77B, J.H.S. No. 8905).
*Inside bottom color of upper labium.*—Strong reddish purple (R.H.S. 77B, J.H.S. No. 8905).
*Inside color of lower part of lower labium.*—Deep reddish purple (R.H.S. 78A, J.H.S. No. 8907).
*Inside color of middle part of lower labium.*—Strong reddish purple (R.H.S. 77B, J.H.S. No. 8905).
*Inside base color of lower labium.*—Strong reddish purple (R.H.S. 77B, J.H.S. No. 8905).
*Inside margin color of petal.*—Strong reddish purple (R.H.S. 77B, J.H.S. No. 8905).
*Outside color of corolla tube.*—Strong reddish purple (R.H.S. 77B, J.H.S. No. 8905).
*Shape of upper labium.*—Narrow.
*Shape of lower labium.*—Wide.
*Hair density on a corolla tube.*—Sparse.
*Hair density on a upper labium.*—Sparse.
*Hair density on a lower labium.*—Sparse.
*Shape of calyx.*—Tubular and in five lanceolate segments.
*Length of calyx.*—Approximately 14 mm.
*Width of calyx.*—Approximately 1.8 mm.
*Color of calyx.*—Moderate yellow green (R.H.S. 146C, J.H.S. No. 3513).
*Anthocyanin pigmentation on calyx.*—Absent.
*Flower fragrance.*—Present; similar to mint.
*Flowering period.*—May to October.

Physiological and ecological characteristics:
*Resistance to cold.*—Strong.
*Resistance to heat.*—Strong.
*Pest resistance.*—Strong.
*Disease resistance.*—Strong The botanical characteristics of the male parent '971' plant are as follows:

Plant:
*Plant form.*—Conical.
*Plant height.*—Approximately 300 mm.

Branches:
*Branch color.*—Moderate yellow green (R.H.S. 146D, J.H.S. No. 3511) on young branches, brown (R.H.S. 165A, J.H.S. No. 1608) on mature branches, and grey-brown (R.H.S. 199D, J.H.S. No. 1918) on very old branches.
*Branch texture.*—Smooth to slightly rough on young branches, and slightly rough on mature and very old branches.
*Lenticels.*—Absent.
*Presence of stem hairs.*—Sparse.
*Density of main stem branching.*—Extensive.
*Length of internode.*—Approximately 5 mm.

Leaf:
*Phyllotaxis.*—Opposite.
*Leaf shape.*—Elliptic-obovate.
*Shape of leaf margin.*—Obtuse serrate.
*Leaf attaching angle to stem.*—Horizontal.
*Leaf length.*—Approximately 8 mm.
*Leaf width.*—Approximately 10 mm.
*Color of leaf upper side.*—Grayish green (R.H.S. 189A, J.H.S. No. 4012).
*Color of leaf reverse side.*—Pale green (R.H.S. 190A, J.H.S. No. 4011).
*Leaf thickness.*—Approximately 0.5 mm.
*Hair density on a leaf upper side.*—Sparse.
*Petiole length.*—Approximately 5.0 mm.
*Leaf fragrance.*—Present; similar to mint.

Flower:
*Inflorescence type.*—Verticillaster.
*Length of Spike/Cluster.*—Approximately 21 mm.
*Length of flower interval.*—Approximately 2.2 mm.
*Number of flowers in a inflorescence.*—Approximately 10.
*Corolla form.*—Lobed and bilabiate.
*Vertical diameter of flower.*—Approximately 6 mm.
*Horizontal diameter of flower.*—Approximately 8 mm.
*Length of flower.*—Approximately 14 mm.
*Length of corolla tube.*—Approximately 12 mm.
*Width of corolla tube.*—Approximately 5 mm.
*Inside color of upper part of upper labium.*—Pale purplish pink (R.H.S. 75D, J.H.S. No. 8902).
*Inside color of middle part of upper labium.*—Light purplish pink (R.H.S. 75B, J.H.S. No. 8903).
*Inside bottom color of upper labium.*—Pale purplish pink (R.H.S. 75D, J.H.S. No. 8902).
*Inside color of lower part of lower labium.*—Pale purplish pink (R.H.S. 75D, J.H.S. No. 8902).
*Inside color of middle part of lower labium.*—Pale purplish pink (R.H.S. 75D, J.H.S. No. 8902).
*Inside base color of lower labium.*—Pale purplish pink (R.H.S. 75D, J.H.S. No. 8902).
*Inside margin color of petal.*—Pale purplish pink (R.H.S. 75D, J.H.S. No. 8902).
*Outside color of corolla tube.*—Light purplish pink (R.H.S. 75B, J.H.S. No. 8903).
*Shape of upper labium.*—Narrow.
*Shape of lower labium.*—Wide.
*Hair density on a corolla tube.*—Sparse.
*Hair density on a upper labium.*—Sparse.
*Hair density on a lower labium.*—Sparse.
*Shape of calyx.*—Tubular and in five lanceolate segments.
*Length of calyx.*—Approximately 5.5 mm.
*Width of calyx.*—Approximately 2.0 mm.
*Color of calyx.*—Light purplish gray (R.H.S. 189C, J.H.S. No. 8614).
*Anthocyanin pigmentation on calyx.*—Sometimes present.
*Flower fragrance.*—Present; similar to mint.
*Flowering period.*—May to November.

Physiological and ecological characteristics:
*Resistance to cold.*—Strong.
*Resistance to heat.*—Strong.
*Pest resistance.*—Strong.
*Disease resistance.*—Strong This new and distinct 'Sunminbu' variety was asexually reproduced by cuttings at the aforementioned Oumi Nursey Center of Suntory Limited., located at 863-1, Aza-Iketani, Oomori-cho, Youkaichi-shi, Shiga-ken, Japan, and the homogeneity and stability thereof were confirmed.

SUMMARY OF THE VARIETY

A new variety of *Hesperozygis myrtoides*×*Hesperozygis dimidiata* plant is provided which exhibits:

(a) A conical growth habit with abundant branching,
(b) Forms in abundance attractive light purple verticillaster blossoms which display a fragrance similar to mint,
(c) Forms branches that initially are green and change to brown as they mature,
(d) propagates well by the use of cuttings, and
(e) Possesses the ability to be grown as attractive ornamentation in pots.

BRIEF DESCRIPTION OF THE PHOTOGRAPHS

FIG. 1 shows a flowering 'Sunminbu' plant of the present invention while growing in a pot.

Figure 2:
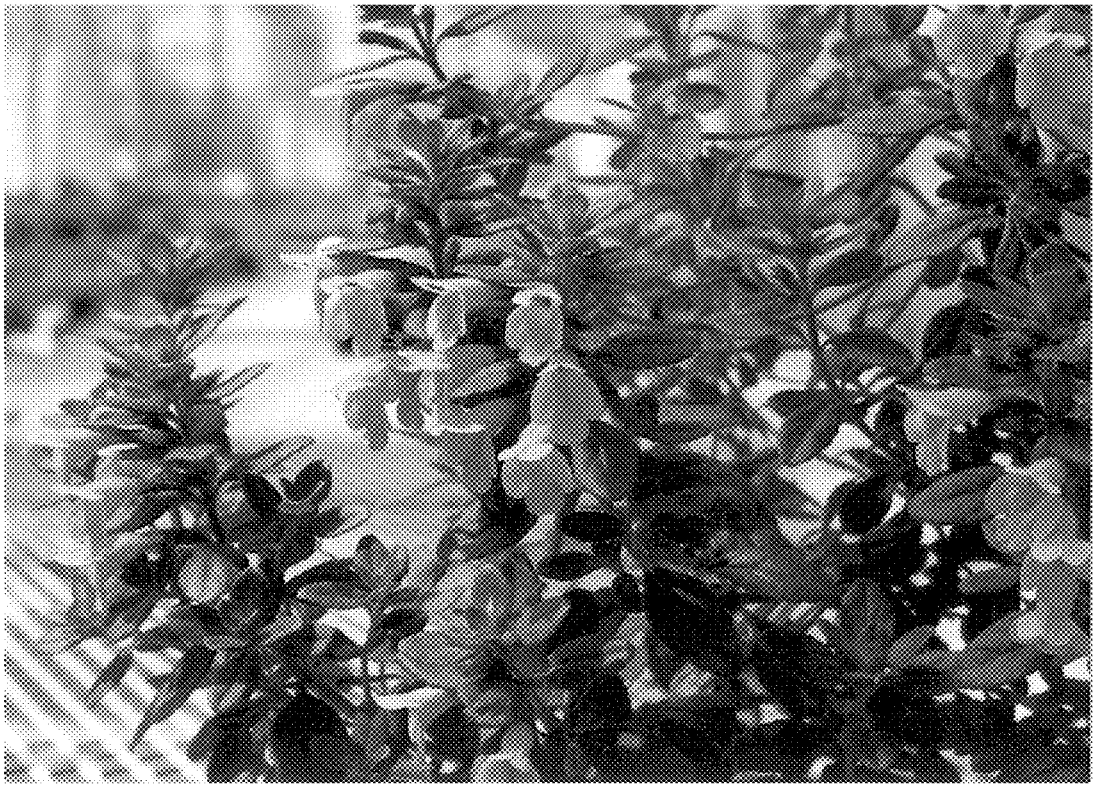

FIG. 2 shows a closer view of the flowers and foliage of the 'Sunminbu' variety. As described in detail hereafter, the blossom coloration of the new variety is pale purple. The more pink-violet blossom coloration shown in the photographs is believed to be attributable to the lighting conditions when the photographs were obtained. Accordingly, see the more accurate blossom color designations for the new variety provided herein where reference is made to standard color charts.

DESCRIPTION OF THE VARIETY

The botanical characteristics of the new and distinct 'Sunminbu' variety are as follows:

Plant:
- *Plant form.*—Conical.
- *Plant Size.*—When grown in a pot having a diameter of 40 cm. in a greenhouse at Youkaichi-shi, Shiga-ken, Japan, a three year-old plant commonly has a height of approximately 50 cm and a width of approximately 50 cm.

Branches:
- *Branch color.*—Varies from green to brown to tan depending on the age. Moderate yellow green (R.H.S. 146C, J.H.S. No. 3513) on young branches, brown (R.H.S. 165A, J.H.S. No. 1608) on mature branches, and tan (R.H.S. 165C, J.H.S. No. 1911) on very old branches.
- *Branch texture.*—Smooth to slightly rough on young branches, and slightly rough on mature and very old branches.
- *Lenticels.*—Absent.
- *Branch cross-section.*—Round.
- *Presence of branch hairs.*—Sparse.
- *Density of branching.*—Substantial (as illustrated).
- *Length of internode.*—Approximately 20 mm.

Leaf:
- *Phyllotaxis.*—Opposite.
- *Leaf shape.*—Elliptic-oblanceolate.
- *Shape of leaf margin.*—Obtuse serrate.
- *Leaf attaching angle to stem.*—Horizontal.
- *Leaf length.*—Approximately 24.5 mm.
- *Leaf width.*—Approximately 11.2 mm.
- *Color of leaf upper side.*—Dark olive green (R.H.S. 139A, J.H.S. No. 3708).
- *Color of leaf upper side.*—Moderate yellow green (R.H.S. 146B, J.H.S. No. 3514).
- *Leaf thickness.*—Approximately 0.5 mm.
- *Hair density on a leaf upper side.*—Sparse.
- *Petiole length.*—3.0 mm.
- *Petiole color.*—Moderate yellow green (R.H.S. 146B, J.H.S. 3514).
- *Leaf fragrance.*—Present; similar to mint.

Flower:
- *Inflorescence type.*—Verticillaster borne in the upper leaf axils commonly with three flowers per axil.
- *Length of Spike/Cluster.*—Approximately 75 mm.
- *Length of flower interval.*—Approximately 10 mm.
- *Number of flowers in a inflorescence.*—Approximately 60 on average on a plant having an age of approximately 7 months from cutting and a height of approximately 38 cm.
- *Corolla form.*—Lobed and bilabiate. The blossoms do not vary with the position on the plant. All blossoms are verticillaster.
- *Vertical diameter of flower.*—Approximately 9 mm.
- *Horizontal diameter of flower.*—Approximately 13 mm.
- *Length of flower.*—Approximately 20 mm.
- *Length of corolla tube.*—Approximately 17 mm.
- *Width of corolla tube.*—Approximately 5 mm.
- *Inside color of upper part of upper labium.*—Light purple (R.H.S. 85B, J.H.S. No. 8303).
- *Inside color of middle part of upper labium.*—Light purple (R.H.S. 85B, J.H.S. No. 8303).
- *Inside bottom color of upper labium.*—Light purple (R.H.S. 85B, J.H.S. No. 8303).
- *Inside color of lower part of lower labium.*—Light purple (R.H.S. 85B, J.H.S. No. 8303).
- *Inside color of middle part of lower labium.*—Brilliant purple (R.H.S. 86D, J.H.S. No. 8305).
- *Inside bottom color of lower labium.*—Light purple (R.H.S. 85B, J.H.S. No. 8303).
- *Inside margin color of petal.*—Light purple (R.H.S. 85B, J.H.S. No. 8303).
- *Outside color of corolla tube.*—Light purple (R.H.S. 85B, J.H.S. No. 8303).
- *Shape of upper labium.*—Narrow and slightly notched at the apex.
- *Shape of lower labium.*—Lobed (as illustrated in FIG. 2).
- *Hair density on a corolla tube.*—Present with two lines of hairs within the tube.
- *Hair density on an upper labium.*—Sparse.
- *Hair density on a lower labium.*—Sparse.
- *Shape of calyx.*—Tubular and in five lanceolate segments.
- *Length of calyx.*—Approximately 11.5 mm.
- *Width of calyx.*—Approximately 1.8 m.
- *Color of calyx.*—Moderate yellow green (R.H.S. 146C, J.H.S. No. 3513).
- *Reproductive organs.*—Two stamens having substantially straight filaments and two anthers with fertile anther sacs are separated with a well-developed connective. The single pistil includes a stigma that splits into two segments at the tip.
- *Anthocyanin pigmentation on calyx.*—Absent.
- *Flowering period.*—June to November. The blossoms commonly last approximately 4 days on the plant and approximately 4 days if cut and placed in a vase. Use as a pot plant is primarily contemplated. Pinching is not necessary to ensure the continued production of blossoms.
- *Fruits.*—Achene in form.

Physiological and ecological characteristics:
- *Resistance to cold.*—Has tolerated a temperature of −5° C.
- *Resistance to heat.*—Has tolerated a temperature of 35° C.

*Pest resistance.*—No serious damage by white flies has been observed.

*Disease resistance.*—Good resistance to Phytophthora and rust.

This new 'Sunminbu' plant is most suitable for flower bedding and potting. It additionally is excellent for use as a ground cover.

I claim:

1. A new and distinct *Hesperozygis myrtoides*× *Hesperozygis dimidiata* plant exhibiting the following combination of characteristics:

(a) a conical growth habit with abundant branching, (b) forms in abundance attractive light purple verticillaster blossoms which display a fragrance similar to mint, (c) forms branches that initially are green and change to brown as they mature, (d) propagates well by the use of cuttings, and (e) possesses the ability to be grown as attractive ornamentation in pots;

substantially as illustrated and described.

* * * * *